United States Patent [19]

Barr

[11] Patent Number: Plant 5,659

[45] Date of Patent: Feb. 11, 1986

[54] DWARF NANDINA NAMED MOON BAY

[75] Inventor: William C. Barr, Rosenberg, Tex.

[73] Assignee: Weyerhaeuser Company, Tacoma, Wash.

[21] Appl. No.: 559,300

[22] Filed: Dec. 8, 1983

[51] Int. Cl.[4] ..... A0H1 5/12

[52] U.S. Cl. ..... Plt./54

[58] Field of Search ..... Plt./54

*Primary Examiner*—Robert E. Bagwill

[57] ABSTRACT

A freely branching dwarf nandina plant having a compact, globose habit.

4 Drawing Figures

The present invention relates to a new and distinct plant variety of *Nandina domestica* (Thunberg), commonly known as Heavenly Bamboo, in the Berberidaciae family.

This new variety was discovered at Hines Wholesale Nurseries, P.O. Box 42284, Houston, Tex., 77242. The new variety originated as a chance seedling in a seedling population of *Nandina domestica.* The plant was selected and isolated as a distinctive form for further evaluation. The new variety has been reproduced numerous times by asexual propagation (vegetative cuttings). Several hundred plants exist. Each of the progeny exhibits identical characteristics to the original mother plant, establishing the variety as reproducible and true to type.

This new variety has many desirable, distinctive characteristics which render it unique from the common species. The overall appearance of the new variety is a dwarf symmetrical, tight globular shape. The plant does not appear to spread by rhizomes, rather, it branches freely from the basal and lateral buds developing multiple ascending stems leading to a globular shape. The foliage is held tightly erect and occurs in a high density fashion. The individual leaf is 2–3 pinnately compound. The individual leaflet is lanceolate and sharply concave. The leaves upon emergence are yellow green, maturing to medium green color. Fall coloration ranges from orange through red, being more intense in cold temperatures.

The accompanying color photographs serve to illustrate the new variety wherein:

FIG. 1 is a color photograph of an unpruned individual plant of the new variety, growing in a 5-gallon container at an age of 22 months from a cutting.

FIG. 2. is a side by side comparison of the new variety, shown on the left, with an average seedling of the species; both plants are in 5-gallon containers at an approximate age 2 years.

DETAILED PLANT DESCRIPTION

Figure 1:
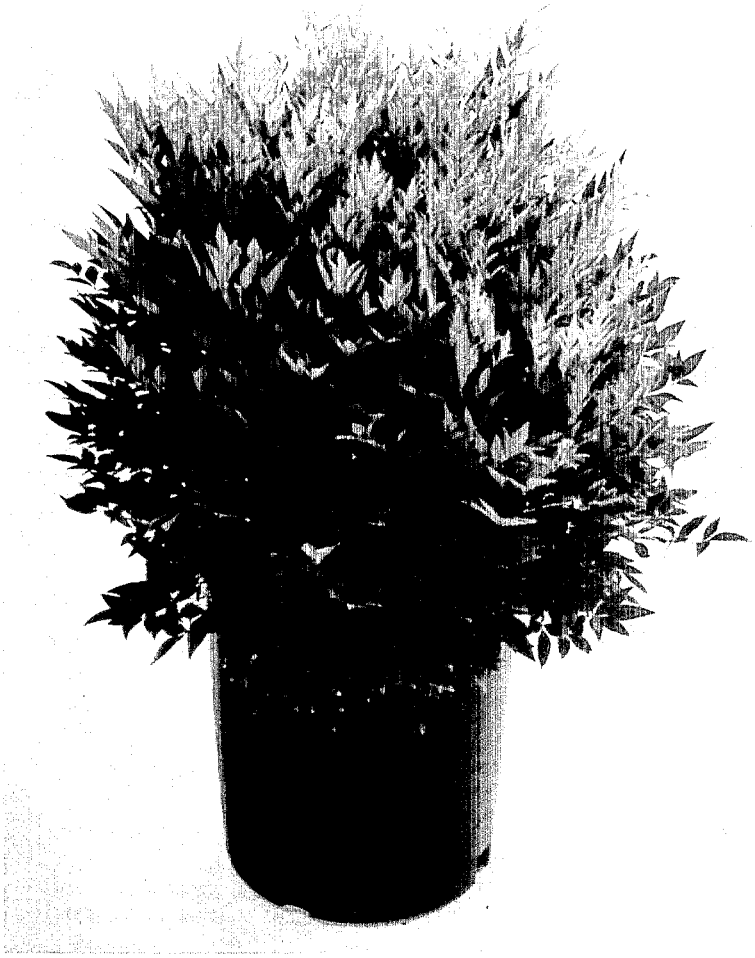
Figure 2:
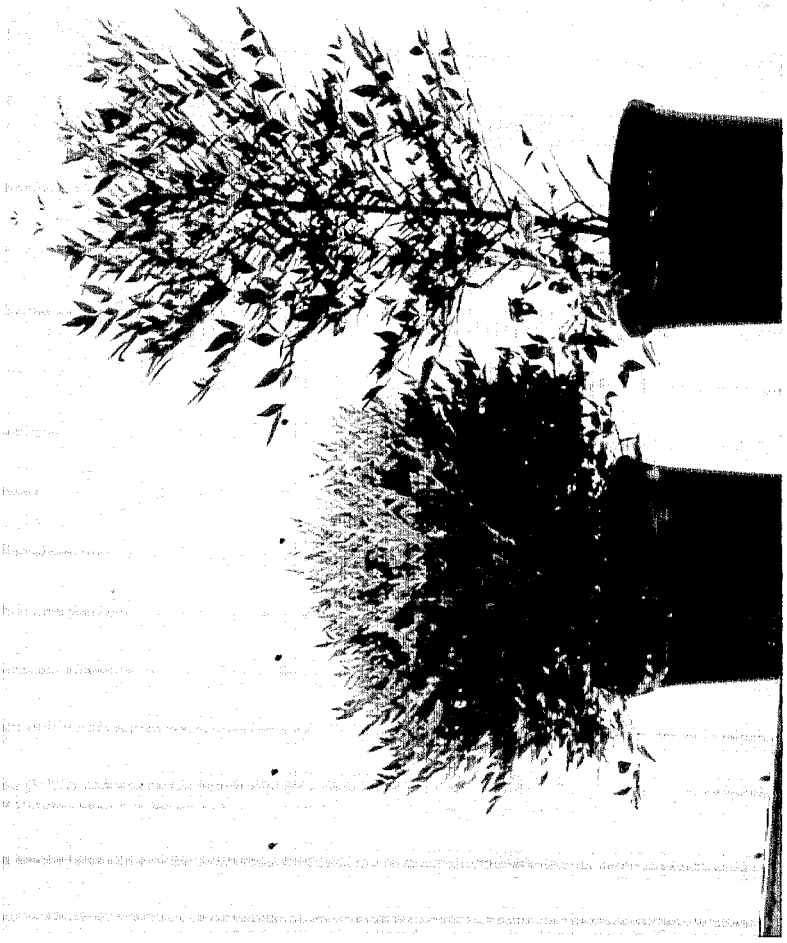
Figure 3:
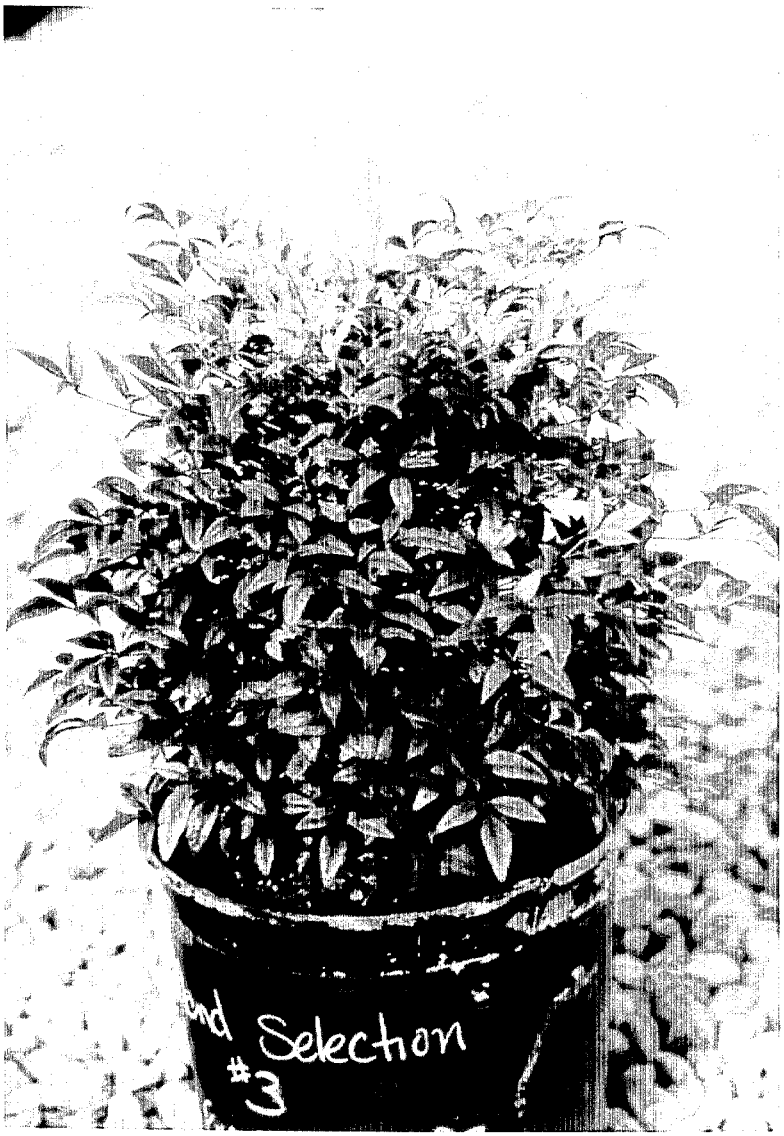
FIG. 3 is a photograph showing the winter coloration of the new variety. This is the same plant as in FIG. 1 but in a 2-gallon container at an age of 16 months.
Figure 4:
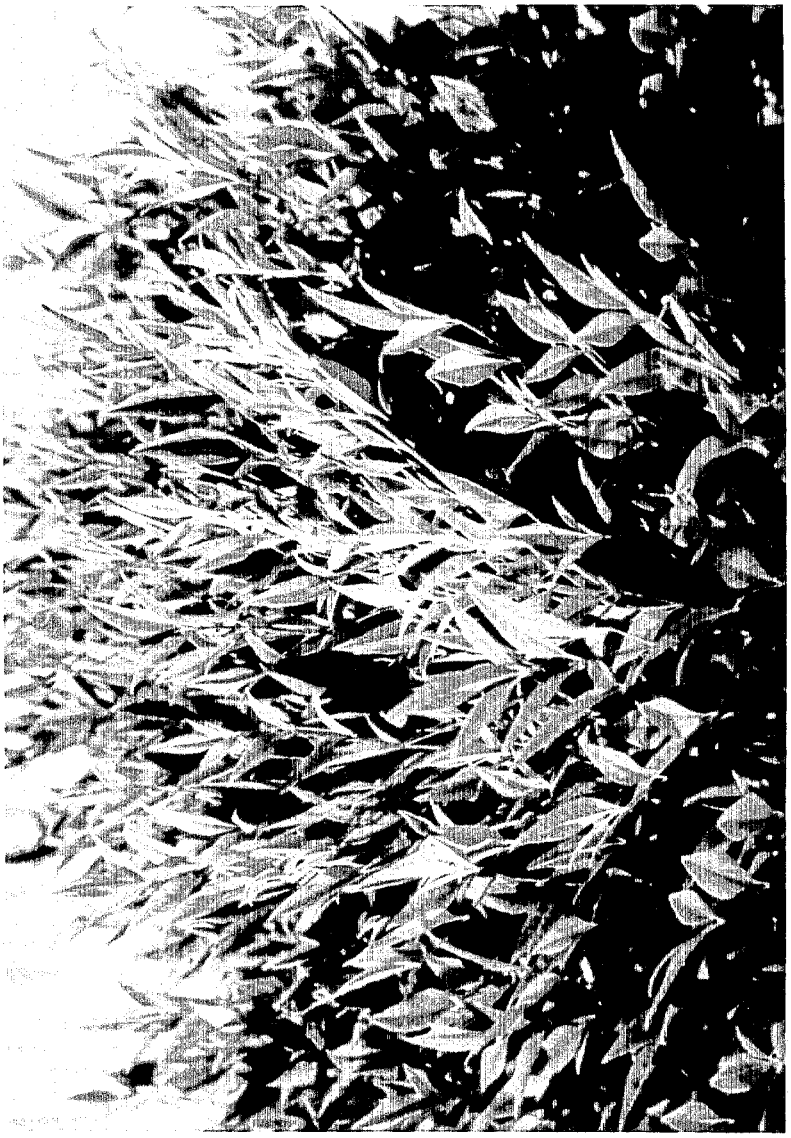
FIG. 4 is a close-up of the new variety's foliage.

Name: *Nandina domestica globosa minor* 'Moon Bay.'

Parentage: A chance seedling in a population of *Nandina domestica.*

Size: Ultimate height is unknown, as no specimen has reached full maturity. Present indications are that the full height will not exceed 50 centimeters and may be less.

Growth habit: Dwarf, symmetrical, tight globular shape. Branches freely from basal and lateral buds developing multiple upright stems with ascending petiole, rachis, petiolule and leaflets. The cultivar does not appear to spread by rhizones.

Leaves:

Foliage:

*Arrangement.*—Alternate, 2–3 pinnately compound, evergreen.

*Size.*—From stem to rachis leaflet tip=19 cm to 26.7 cm (the size may vary depending on the age of the plant and the cultural conditions).

*Shape & form.*—Leaflets are elliptic-lanceolate, sharply concave, ascending.

*Leaflet width.*—(15 count average) 6.4 to 12.7 mm.

*Leaflet length.*—(15 count average) 12.7 to 5.1 mm.

*Stem form.*—Upright.

*Margins.*—Entire, apex acute, surface glabrous.

Texture: Medium.

Flowers: None have been observed; for the species they are white, perfect, borne in erect, terminal panicles.

Disease and insect resistance: No disease or insect problems have occurred requiring other than normal nursery spraying practices common to all nandinas.

Climatic range: In containers has withstood temperature ranging from 20° to 102° F. without any harmful effects. While this specific plant has not been exposed to temperatures lower than 20° F., it is derived from a plant species which is hardy Zone 6 USDA, where low temperatures range from 0° to 10° F.

Color: Mature leaf color, in The Royal Horticultural Society Colour Chart, is under Fan 3, No. 137, Green Group No. A and B. Emerging foliage is under Fan 3, No. 145 No. A. Fall coloration ranges in varying degree from orange through red, being more intense in cold temperatures.

Characteristics: *Nandina domestica* 'Moon Bay' differs from other nandina varieties because of the following major characteristics;

*Form.*—Symmetrical, compact, globose, erect ascending leaflets.

*Height.*—50 cm (1½') or less.

*Color.*—Bright lime-green emerging leaves in spring and summer.

*Branching habit.*—Branches freely from basal and lateral buds. Does not spead by rhizomes as does *Nandina domestica.*

Other *Nandina domestica* Varieties Compared to 'Moon Bay'.

Characteristics & Differences

*Nandina domestica:* 1.8 m lacy foliage, not compact. Spreads by rhizomes.

*N.d.* 'Compacta': 1.2–1.5 m. Leaves descending with an arched habit.

*N.d.* 'Compacta Nana' (also sold as 'Nana' or 'Pygmaea'): 0.3–12. m. Dense, small, broad leaves.

*N.d.* 'Harbour Dwarf' (also known as 'Nana'): Horizontal spreading habit. Lacy leaflets are slightly concave but not ascending. Spreads by rhizomes.

*N.d.* 'Nana Purpurea' (also sold as 'Compacta Nana'): Foliage is coarse, broad and cupped. Average length (20 count) 55.2 mm. Average width (20 count) 23.9 mm.

What is claimed is:

1. A new and distinct plant variety of *Nandina domestica* as shown and described, which is principally characterized by its dwarf, symmetrical, tight globular shape; freely branching from basal and lateral buds developing multiple ascending stems; foliage held tightly erect, yellow-green to medium green in color; and a mature height smaller than the standard species.

* * * * *